United States Patent
Mandan et al.

(10) Patent No.: US 10,800,974 B2
(45) Date of Patent: Oct. 13, 2020

(54) PROCESS FOR PRODUCING CRUDE BIO-OIL

(71) Applicant: RELIANCE INDUSTRIES LIMITED, Mumbai, Maharashtra (IN)

(72) Inventors: Chidambaram Mandan, Tamil Nadu (IN); Balakrishnan Madhesan, Tamil Nadu (IN); Ramesh Bhujade, Maharashtra (IN); Ajit Sapre, Maharashtra (IN)

(73) Assignee: RELIANCE INDUSTRIES LIMITED, Mumbai (IN)

( * ) Notice: Subject to any disclaimer, the term of this patent is extended or adjusted under 35 U.S.C. 154(b) by 0 days.

(21) Appl. No.: 16/348,624

(22) PCT Filed: Nov. 30, 2017

(86) PCT No.: PCT/IB2017/057525
§ 371 (c)(1),
(2) Date: May 9, 2019

(87) PCT Pub. No.: WO2018/116036
PCT Pub. Date: Jun. 28, 2018

(65) Prior Publication Data
US 2019/0359893 A1    Nov. 28, 2019

(30) Foreign Application Priority Data
Dec. 19, 2016  (IN) .............................. 201621023498

(51) Int. Cl.
*C10G 1/08*        (2006.01)

(52) U.S. Cl.
CPC ..... *C10G 1/086* (2013.01); *C10G 2300/1003* (2013.01); *C10G 2300/1014* (2013.01)

(58) Field of Classification Search
None
See application file for complete search history.

(56) References Cited

U.S. PATENT DOCUMENTS

| | | | |
|---|---|---|---|
| 2012/0055077 A1* | 3/2012 | Savage | ..................... C10L 1/02 44/307 |
| 2016/0130504 A1 | 5/2016 | Soni et al. | |

OTHER PUBLICATIONS

International Search Report in International Application No. PCT/IB2017/057525.
Written Opinion of the International Search Authority in International Application No. PCT/IB2017/057525.

* cited by examiner

*Primary Examiner* — Philip Y Louie
(74) *Attorney, Agent, or Firm* — Ladas & Parry LLP

(57) ABSTRACT

The present disclosure relates to a process for producing crude bio oil from biomass. The process involves hydrothermally liquefying a biomass in presence of a catalyst at a temperature in the range of 250° C. to 400° C. and at a pressure in the range of 70 bar to 225 bar, to obtain a product mixture comprising crude bio-oil. This product mixture comprising crude bio-oil is cooled to obtain a cooled mixture; the oil is then separated from the cooled mixture to obtain crude bio-oil and a residue containing the catalyst. Carbon content of crude bio-oil is in the range of 60 wt % to 85 wt %.

9 Claims, No Drawings

PROCESS FOR PRODUCING CRUDE BIO-OIL

RELATED APPLICATION

This application is a national phase entry under 35 USC 371 of International Patent Application No.: PCT/IB2017/057525 filed on Nov. 30, 2017, which claims priority from Indian Application No. 201621023498 filed on Dec. 19, 2016, the disclosures of which are incorporated in their entirety by reference herein.

FIELD

The present disclosure relates to a process for the production of crude bio-oil (CBO).

Definitions

As used in the present disclosure, the following words and phrases are generally intended to have the meaning as set forth below, except to the extent that the context in which they are used to indicate otherwise.

Biomass

The term biomass in the context of the present disclosure means material such as organic waste (including algal mass), urban refuse, wood, agricultural crops or wastes, municipal wastes and the like, which can be used as a source of fuel or energy.

Crude Bio-Oil

The term crude bio-oil used in the context of the present disclosure means an oil or biofuel derived from a biomass and which can be used as an alternative to petroleum fuel.

Homogeneous Catalyst

The term homogeneous catalyst used in the context of the present disclosure means a catalyst that is in the same phase as the reactants or the reaction medium.

BACKGROUND

Economic development demands energy and this demand for energy has historically led to increased environmental pollution. Despite historical competition between "environment" and "energy", the future demands both environmental protection and energy sustainability. As a result, replacement of a major portion of fossil fuels by renewable energy technologies such as biomass based fuels has been studied extensively. Biomass, a renewable energy source, can either be used directly via combustion to produce heat, or indirectly after converting it to various forms of biofuels. Biofuels are derived from biomass and are intended to provide an alternative to petroleum fuels. Conversion of biomass to biofuel can be achieved by different methods, which are broadly classified into thermal, chemical and biochemical methods.

Algae are an important renewable biomass because of their high photosynthetic efficiency, environmental adaptability, short growth cycle, which makes them simple and economical for mass culturing.

Disposal of distillery spent wash, urban refuse, wood, agricultural crops or wastes, municipal wastes, distillery wastes, industrial wastes is a major environmental concern today. However, these waste materials contain remarkable amount of biomass which can be effectively converted to bio-fuel, thereby making them important sources of biofuels.

Hydrothermal liquefaction (HTL) is a technology for converting high-moisture waste biomass into energy dense "crude bio-oil" (CBO) that can be used for direct combustion or refined to obtain transportation grade fuels. HTL, also called as hydrous pyrolysis, is a process for the reduction of complex organic material such as bio-waste or biomass into crude bio-oil and other chemicals. Development of hydrothermal conversion of biomass such as algae, distillery spent wash or industrial waste, in the presence of highly active catalysts will inculcate self-reliance and reduce the dependence on petroleum crude. By developing the above conversion process using commercially available catalyst/chemicals at cheaper prices, CBO can be generated which is compatible with petroleum crude used in the refinery process.

Hydrothermal Liquefaction (HTL) technique, which involves application of heat and pressure to biomass, has the advantage that the lipids and other organic components can be efficiently converted while the biomass is still in a wet condition. During HTL, high moisture biomass is subjected to elevated temperatures and pressures in order to break down and reform the chemical building blocks into crude bio-oil.

Lipids present in the crude bio-oil can be extracted by solvent extraction or by physical extraction. However, such techniques may not be able to extract the lipids completely. In order to make biomass an economically viable alternative for bio crude oil production, the revenues from all their fractions (and not only the lipids) need to be maximized. A temperate and high pressure thermochemical conversion technique that processes the whole of the biomass in order to produce a liquid energy carrier is required.

There is, therefore felt a need to develop a process for the conversion of biomass to crude bio-oil (CBO).

Objects

Some of the objects of the present disclosure, which at least one embodiment herein satisfies, are as follows.

It is an object of the present disclosure to ameliorate one or more problems of the prior art or to at least provide a useful alternative.

It is an object of the present disclosure to provide a process for the production of crude bio-oil.

It is another object of the present disclosure to provide a simple, energy efficient, time saving and high yielding process for the production of crude bio-oil.

It is yet another object of the present disclosure to provide a process which is capable of producing crude bio-oil containing relatively high carbon content.

Other objects and advantages of the present disclosure will be more apparent from the following description, which is not intended to limit the scope of the present disclosure.

SUMMARY

The present disclosure provides a process for producing crude bio-oil from biomass. The process comprises preparing an aqueous biomass slurry having biomass concentration in the aqueous slurry in the range of 5 wt % to 35 wt %. Preferably, biomass concentration in aqueous slurry is in the range of 8 wt % to 16 wt %, more preferably 10 wt %. In accordance with one embodiment of the present disclosure, the aqueous biomass slurry is prepared by mixing biomass with water. In accordance with another embodiment of the present disclosure, the aqueous slurry of biomass is prepared by removing excess water by known means, in order to obtain the slurry having biomass concentration in the range of 8 wt % to 16 wt %, preferably 10 wt %.

The biomass can be selected from the group consisting of algal biomass, distillery spent wash, urban refuse, wood, agricultural crops or wastes, municipal wastes, distillery wastes, industrial wastes. Further, algal biomass can be selected from the group consisting of *Rhodophyta, Chlorophyta, Phaeophyta, Chrysophyta, Cryptophyta, Dinophyta, Tribophyta, Glaucophyta, Spirulina, Nannochloropsis, Chlorella, cyanobacteria, Euglena, Microcystis, Anabaena, Dictyosphaerium, Nodularia, Oscillatoria, Spirogyra, Hydrodictyon, Chara, Nitella, Oedognium, Phormidium* and *filammntous* algae.

A predetermined amount of a catalyst is added to the biomass slurry to form a reaction mixture. In one embodiment of the present disclosure, the catalyst can be a homogeneous catalyst. In accordance with the present disclosure the catalyst can be a compound having ammonium as a cation and an anion selected from the group consisting of a halide, an acetates, a sulfate, a sulphite, a nitrate, a nitrite, a sulphonate, an oleate, and an oxalate. The predetermined amount of the catalyst can be in the range of 5 wt % to 15 wt % with respect to the total weight of biomass. Preferably, the predetermined amount of the catalyst is 10 wt % with respect to the total weight of the biomass.

Further, the biomass slurry can be subjected to hydrothermal liquefaction, which comprises the step of heating the reaction mixture at a temperature in the range of 250° C. to 400° C., at a pressure in the range of 70 bar to 225 bar, under an inert atmosphere, for a time period in the range of 10 minutes to 90 minutes, to obtain a product mixture comprising crude bio-oil. The product mixture comprising crude bio-oil is then cooled to obtain a cooled mixture. The oil is separated from the cooled mixture to obtain crude bio-oil and a residue containing the catalyst. The yield of crude bio-oil is in the range of 30 wt % to 78 wt %.

The process of the present disclosure comprises an additional step of recovering and recycling the catalyst to the process step of forming the reaction mixture.

The crude bio-oil prepared by the process of the present disclosure is characterized by a carbon content in the range of 60 wt % to 85 wt %.

DETAILED DESCRIPTION

Increase in the price for fuels is driven by a number of factors including the depletion of easily accessible petroleum and natural gas deposits, growth of the emerging economies, political instability, and mounting environmental concerns. Increasing energy prices will eventually require a significant restructuring or replacement of a portion of the fossil fuels by renewable sources of energy such as biomass-based fuels. These renewable sources of energy have a much lower environmental impact than the existing non-renewable sources of energy. Micro-organisms such as algae, archaea, bacteria and fungi including *filamentous* fungi, mold and yeast may contain triglycerides up to 80% of their total dry matter content. However, oil from the microbial biomass which is suitable as a precursor for fuel production is scarce in the market. This is mainly due to the lack of efficient and economical methods for providing good quality oil from microbial biomass.

Biomass such as algal biomass, distillery spent wash, urban refuse, or industrial wastes are promising feedstock for producing CBO. Under normal conditions, the lipids can be extracted by solvent extraction or by physical extraction but the process may not be able to extract all the organic components from the biomass. In order to make biomass an economically viable alternative for crude bio-oil production, the revenues from all their fractions (and not only the lipids) need to be maximized. In this context, hydrothermal liquefaction (HTL) appears to be a promising thermochemical conversion technique that processes the whole biomass to produce a liquid energy carrier, the crude bio-oil (CBO). The higher value of the primary product and the lower energy requirements compared to other technologies turn HTL to be a very promising, if not the most promising, conversion technology for biomass conversion.

The present disclosure envisages a process for producing the crude bio-oil from biomass. The process is described herein below.

In the first step, the aqueous slurry of the biomass is prepared, wherein the concentration of the biomass in the aqueous slurry is in the range of 5% to 35%. Preferably, the concentration of the biomass in the aqueous slurry is in the range of 8 wt % to 16 wt %, more preferably 10 wt %.

In accordance with one embodiment of the present disclosure, aqueous slurry of the biomass is prepared by mixing a predetermined amount of biomass with a predetermined amount of water.

In accordance with another embodiment of the present disclosure, the aqueous slurry of biomass is prepared by removing excess water by known means, in order to obtain the slurry having biomass concentration in the range of 8 wt % to 16 wt %, preferably 10 wt %.

In accordance with the embodiments of the present disclosure, the biomass is selected from the group consisting of algal biomass, distillery spent wash, urban refuse, wood, agricultural crops or wastes, municipal wastes, distillery wastes and industrial wastes.

In accordance with one exemplary embodiment of the present disclosure, the biomass is algal biomass.

In accordance with the embodiments of the present disclosure, the algal biomass is selected from the group consisting of, but not limited to, *Rhodophyta, Chlorophytra, Phaeophyta, Chrysophyta, Cryptophyta, Dinophyta, Tribophyta, Glaucophyta, Spirulina, Nannochloropsis, Chlorella, cyanobacteria, Euglena, Microcystis, Anabaena, Dictyosphaerium, Nodularia, Oscillatoria, Spirogyra, Hydrodictyon, Chara, Nitella, Oedognium, Phormidium* and *filamentous* algae.

In accordance with another exemplary embodiment of the present disclosure, the biomass is distillery spent wash.

In accordance with still another exemplary embodiment of the present disclosure, the biomass to is petrochemical sludge.

In the second step, a predetermined amount of at least one catalyst is added to aqueous slurry to form a reaction mixture.

In accordance with the embodiments of the present disclosure, the predetermined amount of the catalyst is in the range of 5% to 15% with respect to the total weight of the biomass. In accordance with the exemplary embodiment of the present disclosure, the predetermined amount of the catalyst is 10% with respect to the total weight of biomass.

In accordance with the present disclosure, the catalyst is cationic or anionic in nature. In accordance with the embodiments of the present disclosure, the catalyst is a homogeneous catalyst. In accordance with the embodiments of the present disclosure, the catalyst is a compound having ammonium as a cation and an anion selected from the group consisting of a halide, an acetate, a sulphate, a sulphite, a nitrate, a nitrite, a sulphonate, an oleate, a sulphate, an oxalate.

In the next step, biomass is subjected to hydrothermal liquefaction (HTL) by heating the reaction mixture at a temperature in the range of 250° C. to 400° C., at a pressure in the range of 70 bar to 225 bar, and under an inert atmosphere, typically nitrogen atmosphere for a time period in the range of 10 minutes to 90 minutes to obtain a product mixture comprising crude bio-oil. The hydrothermal liquefaction (HTL) involves stirring the reaction mixture during the HTL step at a speed in the range of 450 rpm to 550 rpm.

The product mixture comprising crude bio-oil is cooled to obtain a cooled mixture. The oil is then separated from the cooled mixture to obtain crude bio-oil and a residue containing the catalyst. Typically the step of separation of the oil from the cooled mixture is achieved by at least one step selected from the group consisting of, but not limited to, filtration, centrifugation, decantation, adsorption, chromatography, liquid-liquid extraction, and solid-phase extraction.

In the exemplary embodiments of the present disclosure, the yield of crude bio-oil is in the range of 30% to 75%. Further, in accordance with the embodiments of the present disclosure, the carbon content of the crude bio-oil in the range of 60% to 85%.

The catalyst being highly soluble in water is recovered in the aqueous phase from the residue. In accordance with the present disclosure, the catalyst is recycled without any regeneration processes.

In accordance with the present disclosure, the presence of the catalysts assists through its efficient cell wall rupturing functionality and thus a maximum amount of organic components is drawn into the resultant crude bio-oil.

The present disclosure is further described in light of the following experiments which are set forth for illustration purpose only and not to be construed for limiting the scope of the disclosure. The following experiments can be scaled up to industrial/commercial scale and the results obtained can be extrapolated to industrial scale.

EXPERIMENTAL DETAILS

The following experimental procedure was followed to perform the hydrothermal liquefaction of biomass. The type of biomass and type of catalysts were varied and the results are provided in Table 1.

Experiments 1 to 4: Conversion of Algal Biomass to Crude Bio-Oil (CBO)

The experiments 1 to 4 were typically carried out in the absence of the catalyst. The type of algae were varied and selected from the group consisting of *Spirulina, nanochloropsis, Nanochloris*, and *Dictyosphaerium*.

Initially, in a reaction vessel, 20 g of algae was mixed with 115 mL of water to form aqueous slurry. The concentration of algae in aqueous slurry was 20 wt %.

The so obtained slurry was heated at a temperature of 350° C., and at a pressure of 200 bar, under nitrogen atmosphere, under stirring at a speed of 500 rpm for 30 minutes to obtain a product mixture comprising crude bio-oil (CBO).

Further, upon cooling, the product mixture was filtered and separated to obtain crude bio-oil.

The results after hydrothermal liquefaction are summarized in Table-1.

Experiment 5: Conversion of Distillery Spent Wash to Crude Bio-Oil (CBO)

The experiment 5 was typically carried out in the absence of the catalyst.

Initially, in a reaction vessel 100 mL of distillery spent wash was mixed with 900 mL water with the help of mixer to form aqueous slurry.

The so obtained slurry was heated at a temperature of 350° C. and at a pressure of 200 bar, under nitrogen atmosphere, under stirring at a speed of 500 rpm for 30 minutes to obtain a product mixture comprising crude bio-oil (CBO).

Further, the product mixture was cooled, filtered and separated to obtain crude bio-oil.

The results after hydrothermal liquefaction are summarized in Table-1.

Experiment 6: Conversion of Petrochemical Sludge to Crude Bio-Oil (CBO)

The experiment 6 was typically carried out in the absence of the catalyst.

Initially, in a reaction vessel 200 mL of petrochemical sludge was mixed with 800 mL water with the help of mixer to form aqueous slurry.

The so obtained slurry was heated at a temperature of 350° C., and at a pressure of 200 bar, under nitrogen atmosphere, under stirring at a speed of 500 rpm for 30 minutes to obtain a product mixture comprising crude bio-oil (CBO).

Further the product mixture was cooled, filtered and separated to obtain crude bio-oil. The results after hydrothermal liquefaction are summarized in Table-1.

Experiments 7 to 15: Conversion of Algal Biomass to Crude Bio-Oil (CBO)

The experiments 7-15 were typically carried out in the presence of the catalyst.

Initially, in a traction vessel, 23 g of algae was mixed with 115 mL of water to firm an aqueous slurry. The concentration of algae in aqueous slurry was 20 wt %. The type of algae was varied and selected from the group consisting of *Spirulina, nanochloropsis, Nanochloris*, and *Dictyosphaerium*.

Further 2 g of the catalyst, was added to aqueous slurry to form a reaction mixture. The type of catalyst was varied and selected from the group consisting of ammonium chloride, ammonium bromide, ammonium acetate, ammonium sulphate and ammonium phosphate.

The so obtained reaction mixture was heated at a temperature of 350° C., and at a pressure of 200 bar, under nitrogen atmosphere, under stirring at a speed of 500 rpm for 30 minutes to obtain a product mixture comprising a crude bio-oil (CBO).

Further, upon cooling, the product mixture was filtered and separated to obtain crude bio-oil.

The results after hydrothermal liquefaction are summarized in Table-1.

Experiment 16: Conversion of Algal Biomass to Crude Bio-Oil (CBO)

The similar experimental procedure as disclosed in experiments 7 to 15 was followed, except the process was carried out at a temperature of 250° C. and at pressure of 130 bar.

The results after hydrothermal liquefaction are summarized in Table-1.

Experiment 17: Conversion of Algal Biomass to Crude Bio-Oil (CBO)

The similar experimental procedure as disclosed in experiments 7 to 15 was followed, except the process was carried out at a temperature of 300° C. and at pressure of 185 bar.

The results after hydrothermal liquefaction are summarized in Table-1.

Experiment 16: Conversion of Algal Biomass to Crude Bio-Oil (CBO)

The similar experimental procedure as disclosed in experiments 7 to 15 was followed, except the process was carried out at a temperature of 350° C. and at pressure of 205 bar.

The results after hydrothermal liquefaction are summarized in Table-1.

Experiment 19: Conversion of Distillery Spent Wash to Crude Bio-Oil (CBO)

Initially, in a reaction vessel 100 mL of distillery spent wash was mixed with 900 mL water with the help of mixer to form aqueous slurry. Further 10 mg of a ammonium chloride was added to aqueous slurry to form a reaction mixture.

The so obtained reaction mixture was heated at a temperature of 350° C., and at a pressure of 200 bar, under nitrogen atmosphere, for 30 minutes to obtain a product mixture comprising a crude bio-oil (CBO).

Further, the product mixture was cooled, filtered and separated to obtain crude bio-oil.

The results after hydrothermal liquefaction are summarized in Table-1.

Experiment 20: Conversion of Petrochemical Sludge to Crude Bio-Oil (CBO)

Initially, in a reaction vessel 200 mL of petrochemical sludge was mixed with 800 mL water with the help of mixer to form aqueous slurry. Further 10 mg of a ammonium chloride was added to aqueous slurry to form a reaction mixture.

The so obtained reaction mixture was heated at a temperature of 350° C., and at a pressure of 200 bar, under nitrogen atmosphere, for 30 minutes to obtain a product mixture comprising a crude bio-oil (CBO).

Further the product mixture was cooled, filtered and separated to obtain crude bio-oil.

The results after hydrothermal liquefaction are summarized in Table-1.

TABLE 1

The catalyst assisted hydrothermal liquefaction (HTL) of biomass

| Experiments | Biomass | Catalyst | Temperature (° C.) | Pressure (bar) | CBO Yield (%) |
|---|---|---|---|---|---|
| 1 | Spirulina | Nil | 350 | 200 | 46.75 |
| 2 | Nannochloropsis | Nil | 350 | 200 | 58.54 |
| 3 | Nannochloris | Nil | 350 | 200 | 50.02 |
| 4 | Dictyosphaerium | Nil | 350 | 200 | 51.21 |
| 5 | Distillery Spent wash | Nil | 350 | 200 | 28.4 |
| 6 | Petrochemical sludge | Nil | 350 | 200 | 69.7 |
| 7 | Spirulina | Ammonium Chloride | 350 | 200 | 53.00 |
| 8 | Nannochloropsis | Ammonium Chloride | 350 | 200 | 73.05 |
| 9 | Nannochloris | Ammonium Chloride | 350 | 200 | 61.08 |
| 10 | Dictyosphaerium | Ammonium Chloride | 350 | 200 | 65.01 |
| 11 | Nannochloropsis | Ammonium Bromide | 350 | 200 | 72.02 |
| 12 | Nannochloropsis | Ammonium Sulphate | 350 | 200 | 69.89 |
| 13 | Nannochloropsis | Ammonium Nitrate | 350 | 200 | 73.01 |
| 14 | Nannochloropsis | Ammonium acetate | 350 | 200 | 66.54 |
| 15 | Nannochloropsis | Ammonium Phosphate | 350 | 200 | 65.98 |
| 16 | Spirulina | Ammonium Chloride | 250 | 130 | 39 |
| 17 | Spirulina | Ammonium Chloride | 300 | 185 | 41 |
| 18 | Spirulina | Ammonium Chloride | 350 | 205 | 47 |
| 19 | Distillery Spent wash | Ammonium Chloride | 350 | 200 | 31.62 |
| 20 | Petrochemical sludge | Ammonium Chloride | 350 | 200 | 70.2 |

From Table-1, it is observed that the hydrothermal liquefaction of biomass carried out in the presence of the catalyst yielded higher amount of crude bio-oil as compared to the hydrothermal liquefaction of biomass, which was carried out in the absence of the catalyst. The yield of the crude bio-oil obtained using the process of the present disclose is in the range of 30% to 73.5%.

Technical Advancements

The present disclosure described herein above has several technical advantages including, but not limited to, the realization of:

a simple, energy efficient, time saving, and high yielding process for catalyst assisted production of crude bio-oil from biomass:

a process which is capable of producing bio-oil containing high carbon content; and reuse of the catalyst in the next cycle of biomass conversion without affecting the CBO yield.

The embodiments as described herein above, and various features and advantageous details thereof are explained with reference to the non-limiting embodiments in the description. Descriptions of well-known aspects, components and molecular biology techniques are omitted so as to not unnecessarily obscure the embodiments herein.

The foregoing description of specific embodiments so fully reveal the general nature of the embodiments herein, that others can, by applying current knowledge, readily modify and/or adapt for various applications of such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein. Further, it is to be distinctly understood that the foregoing descriptive matter is to be interpreted merely as illustrative of the disclosure and not as a limitation.

Having described and illustrated the principles of the present disclosure with reference to the described embodiments, it will be recognized that the described embodiments can be modified in arrangement and detail without departing from the scope of such principles.

While considerable emphasis has been placed herein on the particular features of this disclosure, it will be appreciated that various modifications can be made, and that many changes can be made in the preferred embodiment without departing from the principles of the disclosure. These and other modifications in the nature of the disclosure or the preferred embodiments will be apparent to those skilled in the an from the disclosure herein, whereby it is to be distinctly understood that the foregoing descriptive matter is to be interpreted merely as illustrative of the disclosure and not as a limitation.

The invention claimed is:

1. A process for producing crude bio-oil from biomass, the process comprising:
    a. preparing an aqueous slurry of the biomass;
    b. adding a predetermined amount of at least one homogenous catalyst to the aqueous slurry to form a reaction mixture, wherein said catalyst is a compound having ammonium as a cation and an anion selected from the group consisting of halide, an acetate, a sulfate, a sulphite, a nitrate, a nitrite, a sulfonate, an oleate and an oxalate:
    c. hydrothermally liquefying (HTL) the reaction mixture by heating at a temperature in the range of 250° C. to 400° C., at a pressure in a range of 70 bar to 225 bar, under stirring at a speed in the range of 450 rpm to 550 rpm, in the presence of an inert gas, for a time period in the range of 10 minutes to 90 minutes, to obtain a product mixture comprising crude bio-oil;
    d. cooling the product mixture to obtain a cooled mixture; and
    e. separating the crude bio-oil from the cooled mixture to obtain crude bio-oil, a residue and aqueous phase containing the catalyst.

2. The process as claimed in claim 1, wherein the concentration of the biomass in the aqueous slurry is in the range of 5 wt % to 35 wt %.

3. The process as claimed in claim 1, wherein the concentration of the biomass in the aqueous slurry is in the range of 8 wt % to 16 wt %.

4. The process as claimed in claim 1, wherein the concentration of the biomass in the aqueous slurry is 10 wt %.

5. The process as claimed in claim 1, wherein the process further comprises an additional step of recovering and recycling the catalyst to the process step (c).

6. The process as claimed in claim 1, wherein the biomass is selected from the group consisting of algal biomass, distillery spent wash, urban refuse, wood, agricultural crops or wastes, municipal wastes, distillery wastes and industrial wastes.

7. The process as claimed in claim 4, wherein the algal biomass is selected from the group consisting of *Rhodophyta, Chlorophyta, Phaeophyta, Chrysophyta, Cryptophyta, Dinophyta, Tribophyta, Glaucophyta, Spirulina, Nannochloropsis, Chlorella, cyanobacteri, Euglena, Microcystis, Anabaena, Dictyosphaerium, Nodularia, Oscilatoria, Spirogyra, Hydrodictyon, Chara, Nitella, Oedognium, Phormidium,* and *filamentous* algae.

8. The process as claimed in claim 1, wherein the predetermined amount of the catalyst is in a range of 5 wt % to 15 wt % with respect to the total weigh of the biomass.

9. The process as claimed in claim 1, wherein the predetermined amount of the catalyst is 10 wt % with respect to the total weight of the biomass.

* * * * *